(12) United States Patent
Spohn et al.

(10) Patent No.: US 7,029,458 B2
(45) Date of Patent: Apr. 18, 2006

(54) FRONT-LOADING SYRINGE ADAPTER FOR FRONT-LOADING MEDICAL INJECTOR

(75) Inventors: Michael A. Spohn, Butler, PA (US); Robert J. Ashcraft, Jr., Butler, PA (US); Craig John Bowser, Ford City, PA (US); P. Eric Pavlik, Natrona Heights, PA (US); Albert John Yarzebinski, Glenshaw, PA (US); David M. Reilly, Glenshaw, PA (US); Joseph B. Havrilla, Pittsburgh, PA (US)

(73) Assignee: MEDRAD, Inc., Indianola, PA (US)

( * ) Notice: Subject to any disclaimer, the term of this patent is extended or adjusted under 35 U.S.C. 154(b) by 70 days.

(21) Appl. No.: 10/065,668

(22) Filed: Nov. 7, 2002

(65) Prior Publication Data

US 2003/0040719 A1    Feb. 27, 2003

Related U.S. Application Data

(60) Continuation of application No. 09/631,422, filed on Aug. 3, 2000, now Pat. No. 6,676,634, which is a division of application No. 09/125,454, filed as application No. PCT/US97/05014 on Mar. 27, 1997, now Pat. No. 6,336,913.

(60) Provisional application No. 60/014,472, filed on Mar. 29, 1996.

(51) Int. Cl.
    *A61M 1/00*    (2006.01)
(52) U.S. Cl. .................. 604/152; 604/228; 604/154
(58) Field of Classification Search ............ 604/154, 604/131, 140, 141, 143, 151, 152, 155, 187, 604/228; 222/334, 251, 386; 403/331, 353, 403/381; 128/DIG. 12

See application file for complete search history.

(56) References Cited

U.S. PATENT DOCUMENTS

| | | | |
|---|---|---|---|
| 3,880,163 A | | 4/1975 | Ritterskamp |
| 4,006,736 A | | 2/1977 | Kranys et al. |
| 4,067,479 A | | 1/1978 | Moline |
| 4,342,312 A | | 8/1982 | Whitney et al. |
| 4,465,473 A | | 8/1984 | Ruegg |
| 4,563,175 A | | 1/1986 | LaFond |
| 4,636,198 A | * | 1/1987 | Stade ................. 604/154 |
| 4,650,465 A | | 3/1987 | Langer et al. |
| 4,677,980 A | | 7/1987 | Reilly et al. |
| 4,695,271 A | | 9/1987 | Goethel |
| 4,911,695 A | * | 3/1990 | Lindner ................. 604/228 |

(Continued)

FOREIGN PATENT DOCUMENTS

EP    0 346 950    12/1989

(Continued)

OTHER PUBLICATIONS

International Search Report for PCT Counterpart Application No. PCT/US97/05014.

(Continued)

*Primary Examiner*—Cris Rodriguez
(74) *Attorney, Agent, or Firm*—Gregory L. Bradley

(57) ABSTRACT

A syringe adapter, which permits use of syringes of various types and sizes to be used with a front-loading injector, includes a piston extension and an adapter face plate. The piston extension includes structure for connecting the piston extension to a drive piston of the injector and a plunger of the syringe. The adapter face plate includes a mounting device for attaching the adapter face plate to an injector and a recess for receiving the distal flange of the syringe. The adapter face plate may also include locking pivot arms for releasably engaging the syringe flange.

55 Claims, 9 Drawing Sheets

U.S. PATENT DOCUMENTS

| | | | |
|---|---|---|---|
| 4,978,335 A | | 12/1990 | Arthur, III |
| 5,007,904 A | * | 4/1991 | Densmore et al. .......... 604/228 |
| 5,269,762 A | | 12/1993 | Armbruster et al. |
| 5,279,569 A | | 1/1994 | Neer et al. |
| 5,300,031 A | * | 4/1994 | Neer et al. .................. 604/154 |
| 5,322,511 A | | 6/1994 | Armbruster et al. |
| 5,383,858 A | * | 1/1995 | Reilly et al. ................. 604/152 |
| 5,456,670 A | | 10/1995 | Neer et al. |
| 5,494,036 A | | 2/1996 | Uber, III et al. |
| 5,520,653 A | * | 5/1996 | Reilly et al. ................. 604/152 |
| 5,535,746 A | | 7/1996 | Hoover et al. |
| 5,643,211 A | * | 7/1997 | Sadowski et al. ........... 604/110 |
| 5,662,612 A | | 9/1997 | Niehoff |
| 5,681,286 A | | 10/1997 | Niehoff |
| 5,741,232 A | | 4/1998 | Reilly et al. |
| 5,779,675 A | | 7/1998 | Reilly et al. |
| 5,788,673 A | * | 8/1998 | Young et al. ................ 604/131 |
| 5,795,333 A | | 8/1998 | Reilly et al. |
| RE35,979 E | * | 12/1998 | Reilly et al. ................. 600/432 |
| 5,865,805 A | | 2/1999 | Ziemba |
| 5,873,861 A | | 2/1999 | Hitchins et al. |
| 5,899,885 A | | 5/1999 | Reilly et al. |
| 5,913,844 A | | 6/1999 | Ziemba et al. |
| 5,928,197 A | | 7/1999 | Niehoff |
| 5,938,639 A | | 8/1999 | Reilly et al. |
| 5,944,694 A | | 8/1999 | Hitchins et al. |
| 5,947,929 A | | 9/1999 | Trull |
| 5,997,502 A | | 12/1999 | Reilly et al. |
| 6,080,136 A | | 6/2000 | Trull et al. |
| 6,082,597 A | | 7/2000 | Beckett et al. |
| 6,241,708 B1 | | 6/2001 | Reilly et al. |
| 6,312,410 B1 | | 11/2001 | Yamamoto |
| RE37,487 E | | 12/2001 | Reilly et al. |
| 6,336,913 B1 | | 1/2002 | Spohn et al. |
| 6,488,661 B1 | * | 12/2002 | Spohn et al. ................ 604/151 |
| 2001/0011163 A1 | | 8/2001 | Nolan, Jr. et al. |

FOREIGN PATENT DOCUMENTS

| | | |
|---|---|---|
| EP | 0 561 122 | 9/1993 |
| EP | 0 567 186 | 10/1993 |
| EP | 0 665 027 | 8/1995 |
| JP | 8-336592 | 12/1996 |
| JP | 9-122234 | 5/1997 |
| WO | WO 95/20410 | 8/1995 |
| WO | WO 95/26211 | 10/1995 |
| WO | WO 97/36635 | 10/1997 |
| WO | WO 99/10032 | 3/1999 |
| WO | WO 01/08727 | 2/2001 |

OTHER PUBLICATIONS

International Search Report for PCT Application No. PCT/US00/20623.

Drawing of Dual Flange Injector Head (publicly disclosed in Jul. 1995).

Medrad MCT/MCT Plus Operation Manual, KMP 810P, Revision B, pp. 4-18 to 4-22 and 6-1 to 6-13 (1991).

Liebel-Flarsheim Company, Angiomat 6000 Digital Injection System Operator's Manual, 600950, Rev 1, pp. 3-6 to 3-8, 4-52 to 4-56 (1990).

Liebel-Flarsheim Company, Angiomat 6000 Contrast Delivery System Brochure (1992).

Liebel-Flarsheim Company, Angiomat CT Digital Injection System Operator's Manual, 600964, pp. 1-3 to 1-4,3-7 to 3-9, 4-37 to 4-39 (1990).

Liebel-Flarsheim Company, Angiomat CT Digital Injection System Operator's Manual, 600964, Rev. A, pp. 1-5, 3-12, 4-18 to 4-51 (1991).

Liebel-Flarsheim Company, CT 9000 Digital Injection System Operators Manual, 800950, Rev. F, pp. 5-24 through 5-38 (1995).

Liebel-Flarsheim Company, CT 900 ADV Digital Injection System Manual, 800961-B, pp. 1-4 to 1-16 (Feb. 1988).

U.S. Appl. No. 09/633,299, filed Aug. 8, 2000.

U.S. Appl. No. 09/814,020, filed Mar. 21, 2001.

* cited by examiner

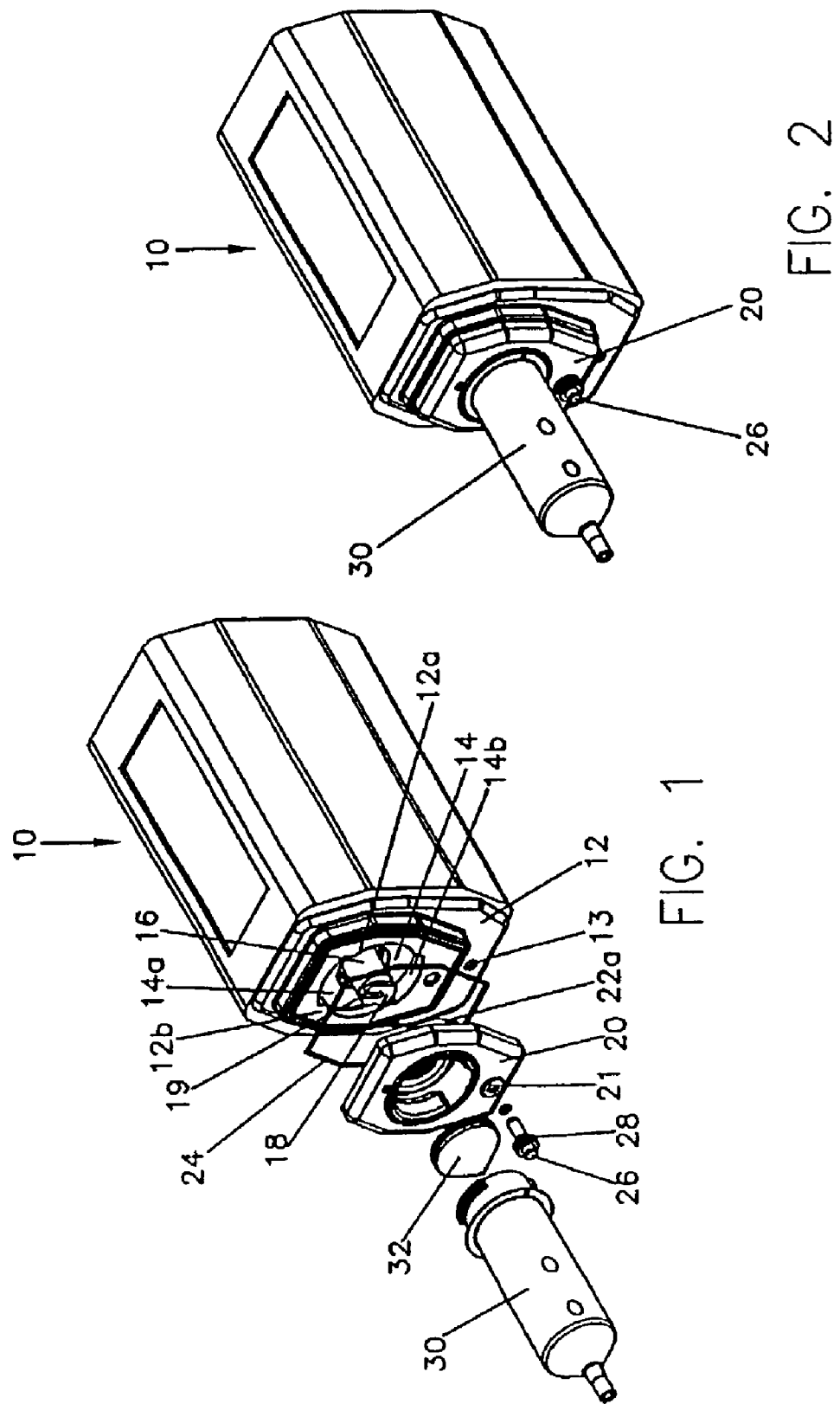

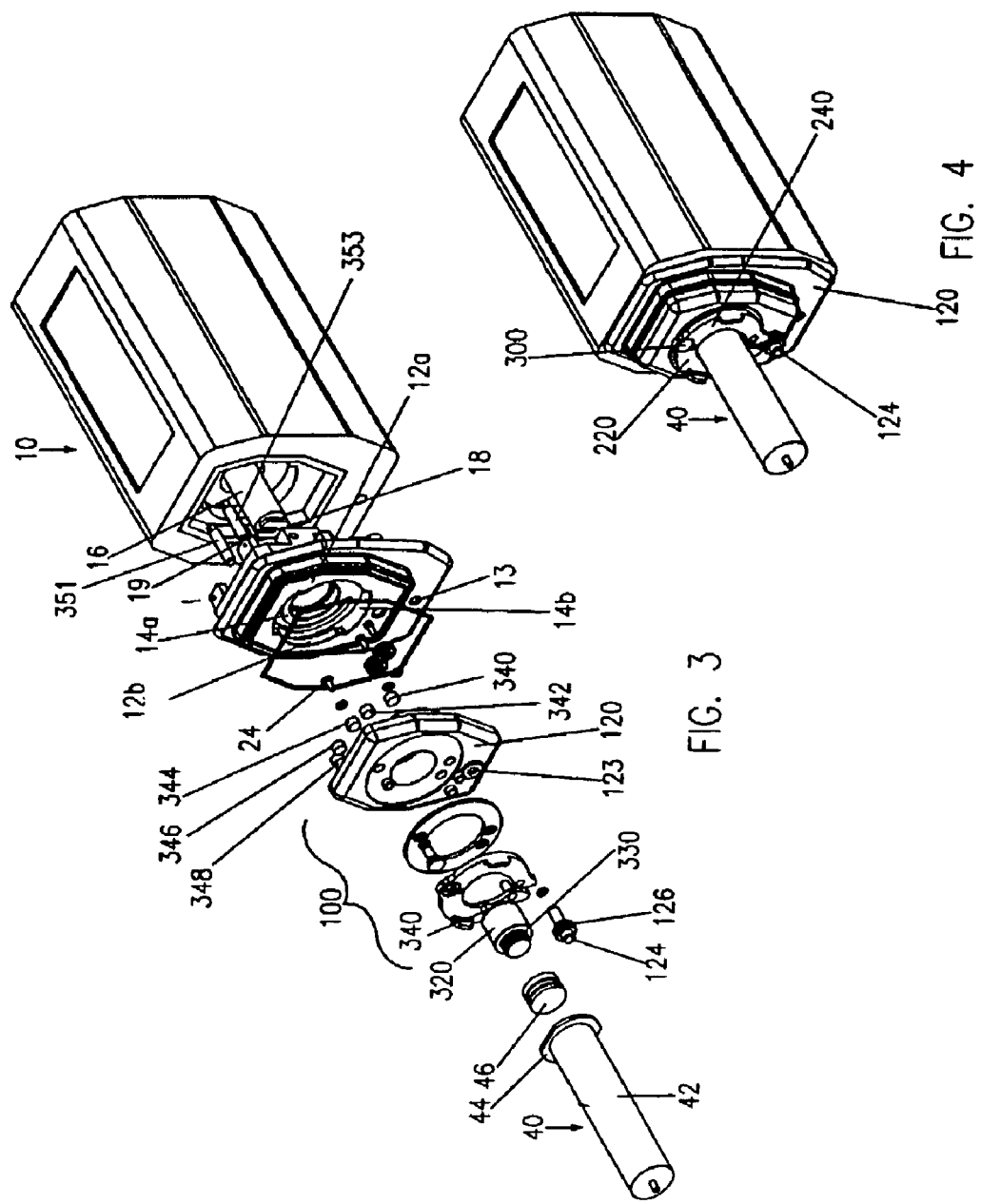

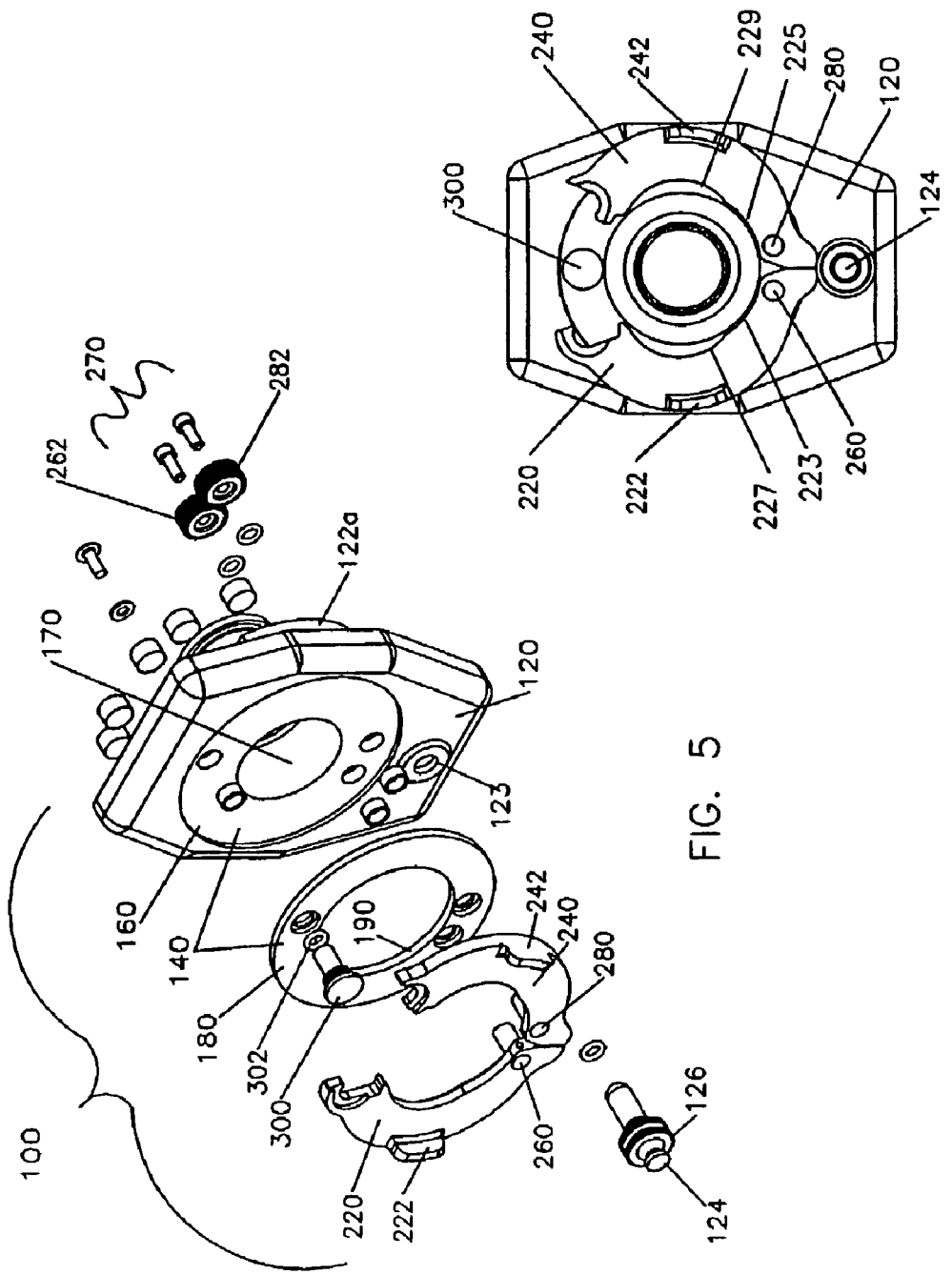

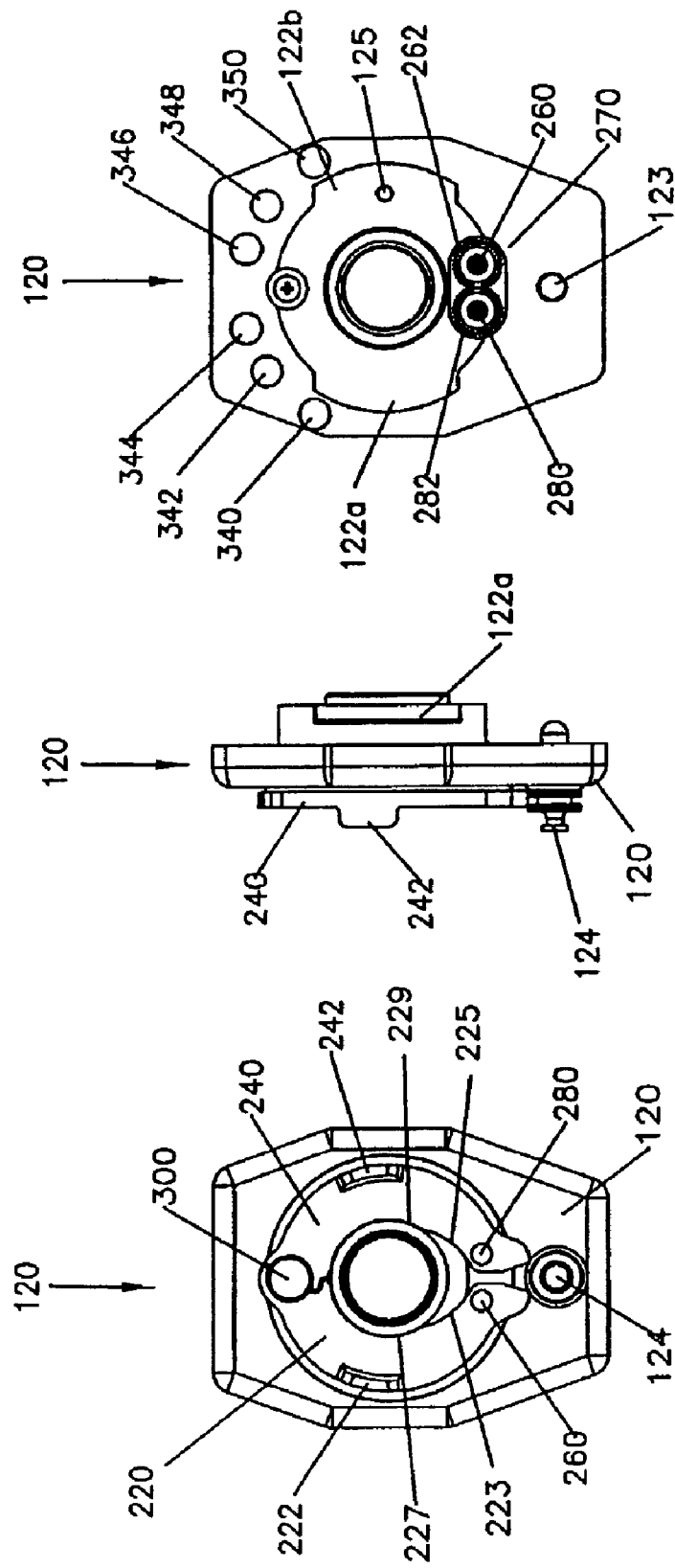

FRONT-LOADING SYRINGE ADAPTER FOR FRONT-LOADING MEDICAL INJECTOR

CROSS REFERENCE TO RELATED APPLICATIONS

This application is a continuation of application Ser. No. 09/631,422, filed on Aug. 3, 2000, which is a divisional of application Ser. No. 09/125,454, filed on Mar. 27, 1997, as PCT International Application No. PCT/US97/05014 designating the United States, now U.S. Pat. No. 6,336,913, which claims the benefit of Provisional Application Ser. No. 60/014,472, filed on Mar. 29, 1996, the contents of which are hereby incorporated by reference.

BACKGROUND OF INVENTION

This invention relates to adapters for releasably attaching and removing syringes to medical injectors, and more particularly to adapters for releasably attaching and removing syringes of various types and sizes to front-loading injectors. Medical injectors and syringes containing fluid, such as contrast media, are commonly used to inject fluid into a patient in a wide variety of diagnostic imaging procedures. Injectors of the front-loading type are often used in such procedures. U.S. Pat. No. 5,383,858, assigned to the assignee of the present invention and fully incorporated herein by reference, provides a detailed description of injectors of the front-loading type and corresponding syringe designs. One advantage of the front-loading injector of U.S. Pat. No. 5,383,858 is that a syringe can readily be loaded onto and removed from the injector head without the need to disconnect the fluid path from the syringe to the patient. Another advantage of the front-loading injector of U.S. Pat. No. 5,383,858 is that the drive means of the injector head may be disengaged and retracted from the syringe plunger without retracting the syringe plunger, thus substantially reducing the risk of withdrawing fluid from the patient after completion of the diagnostic procedure. This feature is also taught in U.S. Pat. No. 4,677,980, assigned to the assignee of the present invention and fully incorporated herein by reference. As discussed in U.S. Pat. No. 5,383,858, a syringe used with a front-loading injector requires a specially designed readily releasable mounting mechanism for securing the syringe to the front wall of the injector head and a specially designed readily releasable mounting mechanism for securing the syringe plunger to the piston head of the injector. These required mounting mechanisms oftentimes increase the cost of the syringes and prohibit the use of syringes of other various types, sizes and configurations with front-loading injectors. Thus, it is desirable to design adapters for use with syringes of various types, sizes and configurations to permit use of these syringes with front-loading injectors.

SUMMARY OF INVENTION

The syringe adapters of the present invention permit use of syringes of various types, sizes and configurations to be used with front-loading injectors, particularly front-loading injectors with or without a removable injector face plate. In one embodiment of the invention, for use with a front-loading injector having a removable injector face plate, the adapter includes an adapter face plate having a readily releasable mounting mechanism for attaching the adapter face plate to the front wall of the injector head after the injector face plate is removed. A removable pin insertable into the adapter face plate and the front wall of the injector head is provided to prohibit the adapter face plate from rotating with respect to front wall of the injector head. The adapter further includes a reducing sleeve formed of a reducing base and reducing edge connected to the proximal surface of the reducing base. The edge and base cooperate to form a recess for receiving the syringe distal flange. The adapter further includes a syringe attachment mechanism, for example, locking pivot arms pivotally attached to the proximal surface of the edge. The reducing edge is preferably made from a material having a low coefficient of friction to permit easy and smooth movement of locking pivot arms. In one embodiment, locking pivot arms are connected by a gear link, which permits simultaneous movement of the arms when only one arm is grasped by the operator to move the arms into an opened or closed position. The inside surface of each pivot arm includes first beveled surfaces to permit reception of the syringe flange when pivot arms are in an open position, and second beveled surfaces to engage the distal end of the syringe body when the pivot arms are in a closed position. Pivot arm ends opposite pivot points are cammed to engage and lock around lock point extending from the reducing edge. The adapter further includes a piston extension to extend the injector drive piston for engagement with the syringe plunger. The piston extension includes means for attaching the extension to the syringe plunger and means for attaching the extension to the injector drive piston. Piston extensions of various diameters and lengths are used to permit use of syringes having various inner diameters and plunger locations. In another embodiment of the invention, for use with a front-loading injector without a removable face plate, the adapter includes an adapter base from which a readily releasable mounting mechanism extends to permit the attachment to and removal of the adapter from the opening in the front wall of the injector head. All of the other adapter elements previously described may be included in this embodiment. For injectors with or without removable face plates, the adapter used may also include signal generating means and the injector may include corresponding sensors which cooperate with one another to indicate to the injector that the adapter is properly attached and to automatically calibrate the injector to adjust, for example, flow rate and pressure.

BRIEF DESCRIPTION OF DRAWINGS

FIG. 1 is an exploded perspective view of a front-loading injector having a removable face plate;

FIG. 2 is an assembled perspective view of the front-loading injector of FIG. 1:

FIG. 3 is an exploded perspective view of a front-loading injector and the first embodiment of the adapter invention;

FIG. 4 is an assembled perspective view of the front-loading injector and the first embodiment of the adapter invention;

FIG. 5 is an exploded view of the first embodiment of the adapter invention;

FIG. 6 is a front view of the first embodiment of the adapter invention in the opened position;

FIG. 7 is a front view of the first embodiment of the adapter invention in the closed position;

FIG. 8 is a side view of the first embodiment of the adapter invention in the closed position;

FIG. 9 is a back view of the first embodiment of the adapter invention in the closed position;

DETAILED DESCRIPTION

Figure 10:
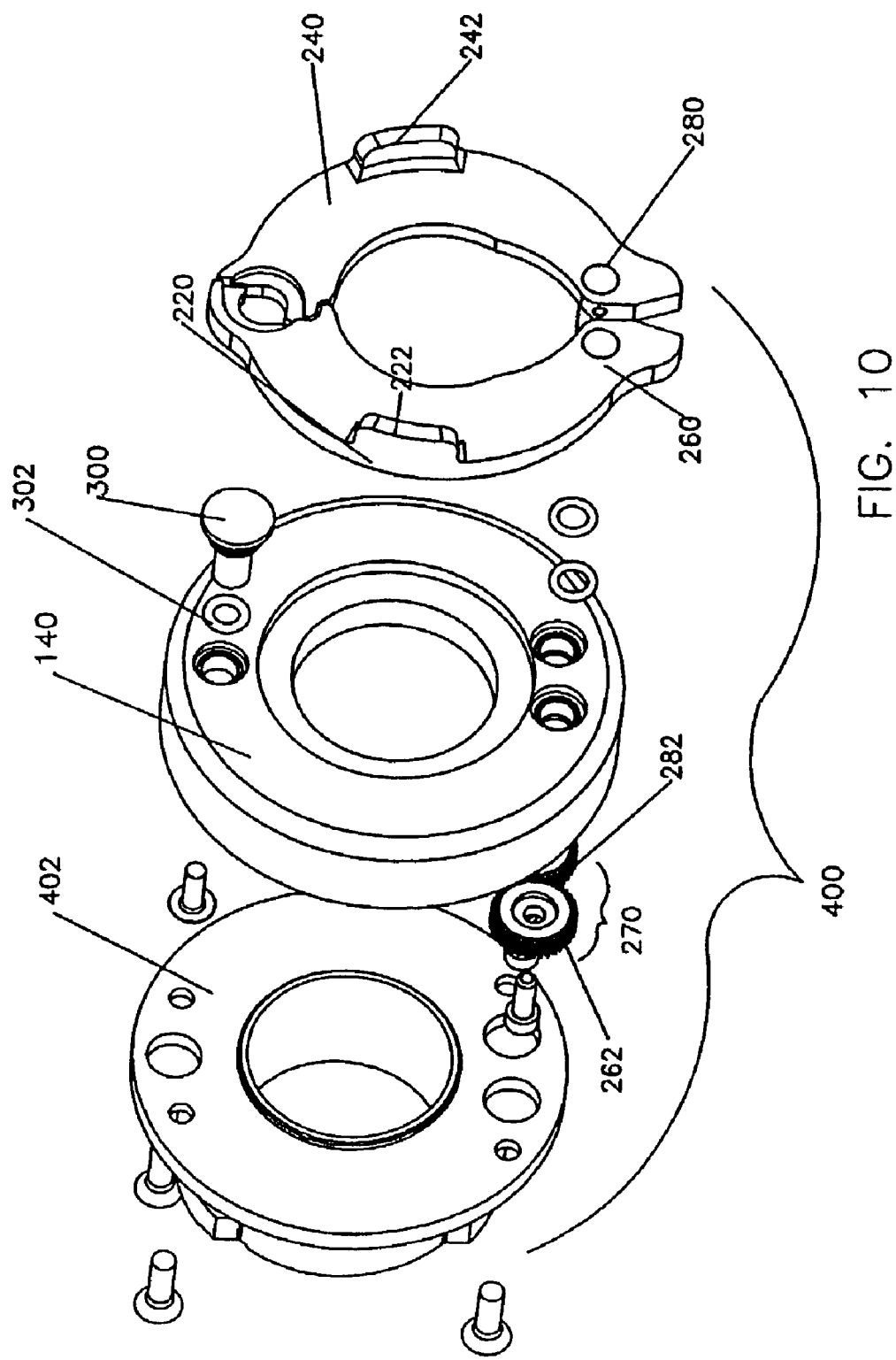
FIG. 10 is an exploded front perspective view of another embodiment of the adapter invention.
Figure 11:
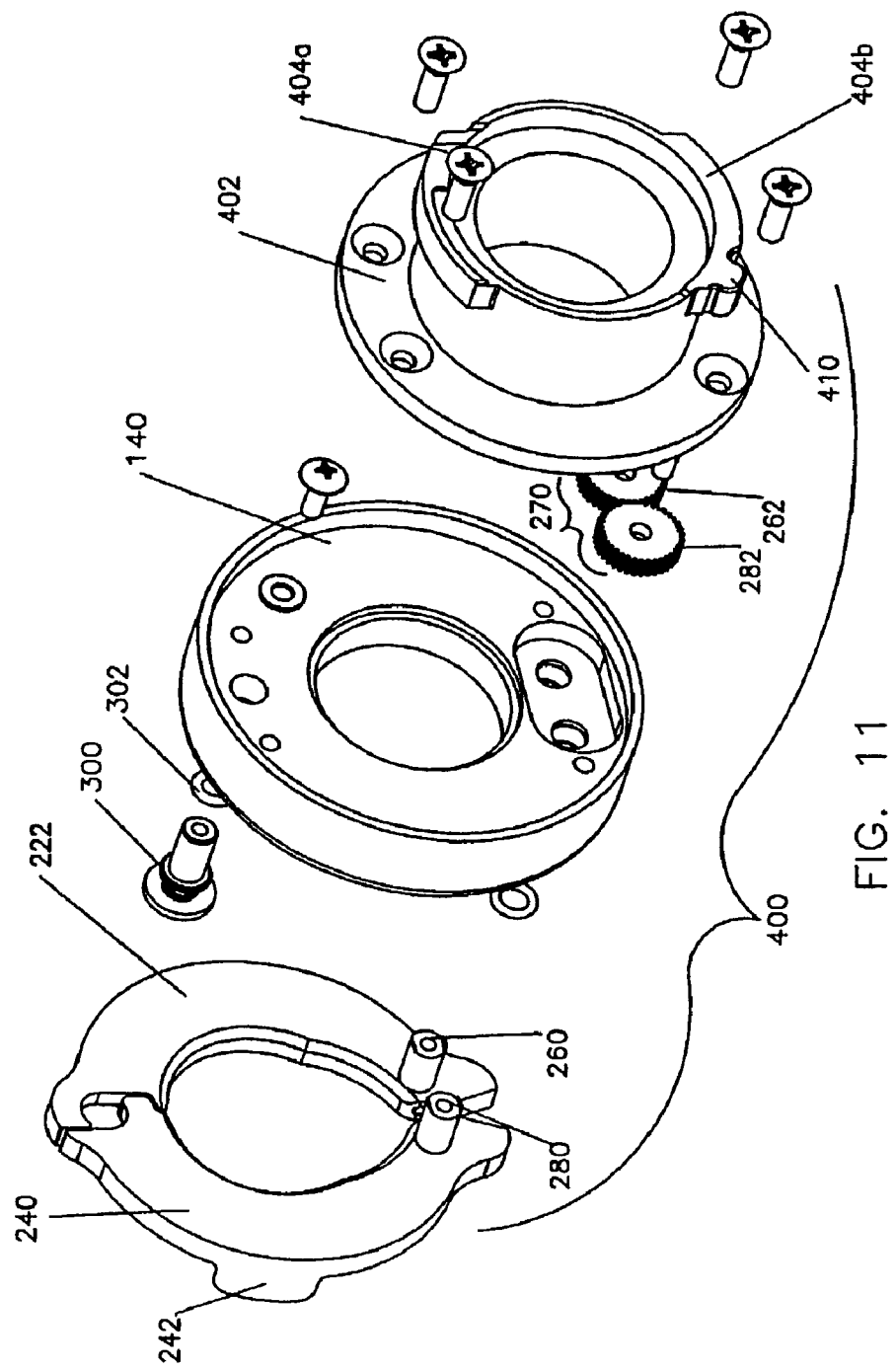
FIG. 11 is an exploded back perspective view of the adapter invention of FIG. 10.
Figure 12:
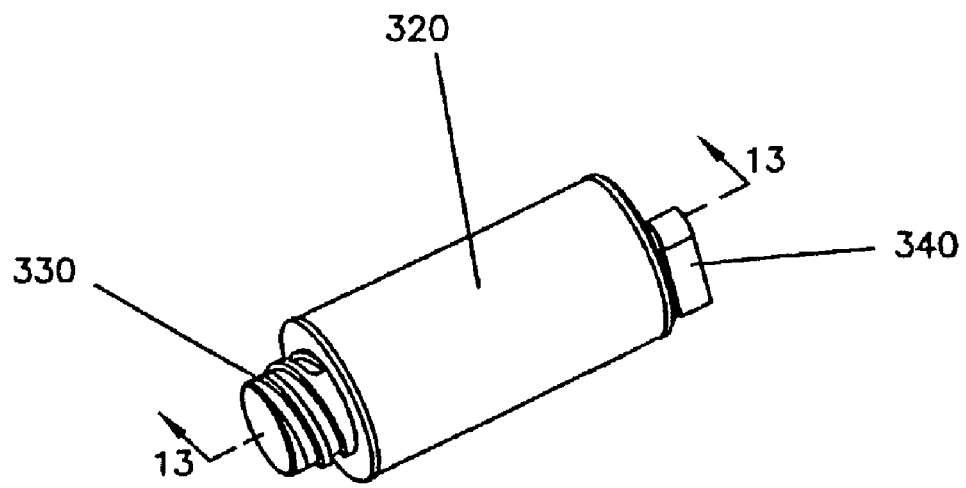
FIG. 12 is a perspective view of one embodiment of a piston extension of the adapter invention.
Figure 13:
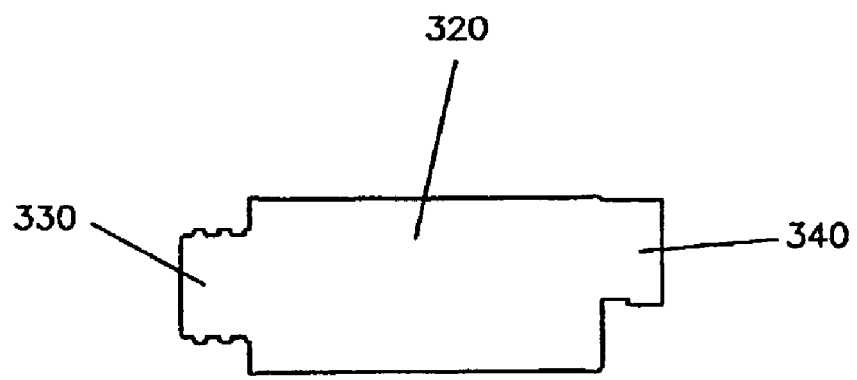
FIG. 13 is a cross-sectional view of the piston extension of the adapter invention taken along line 13—13 of FIG. 12.
Figure 14:
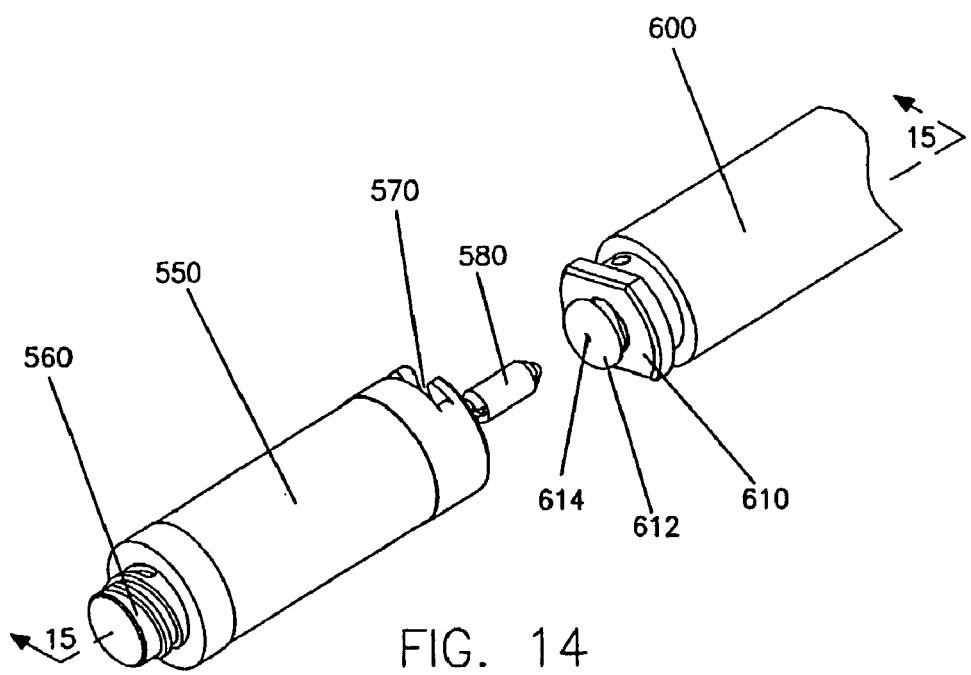
FIG. 14 is a perspective view of another embodiment of a piston extension of the adapter invention.
Figure 15:
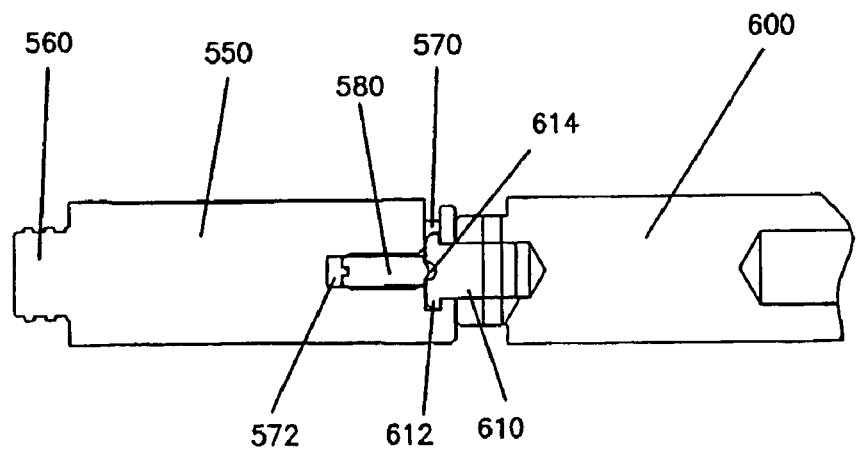
FIG. 15 is a cross-sectional view of the piston extension of the adapter invention taken along line 15—15 of FIG. 14 attached to an injector drive piston of an alternative configuration.
Figure 16:
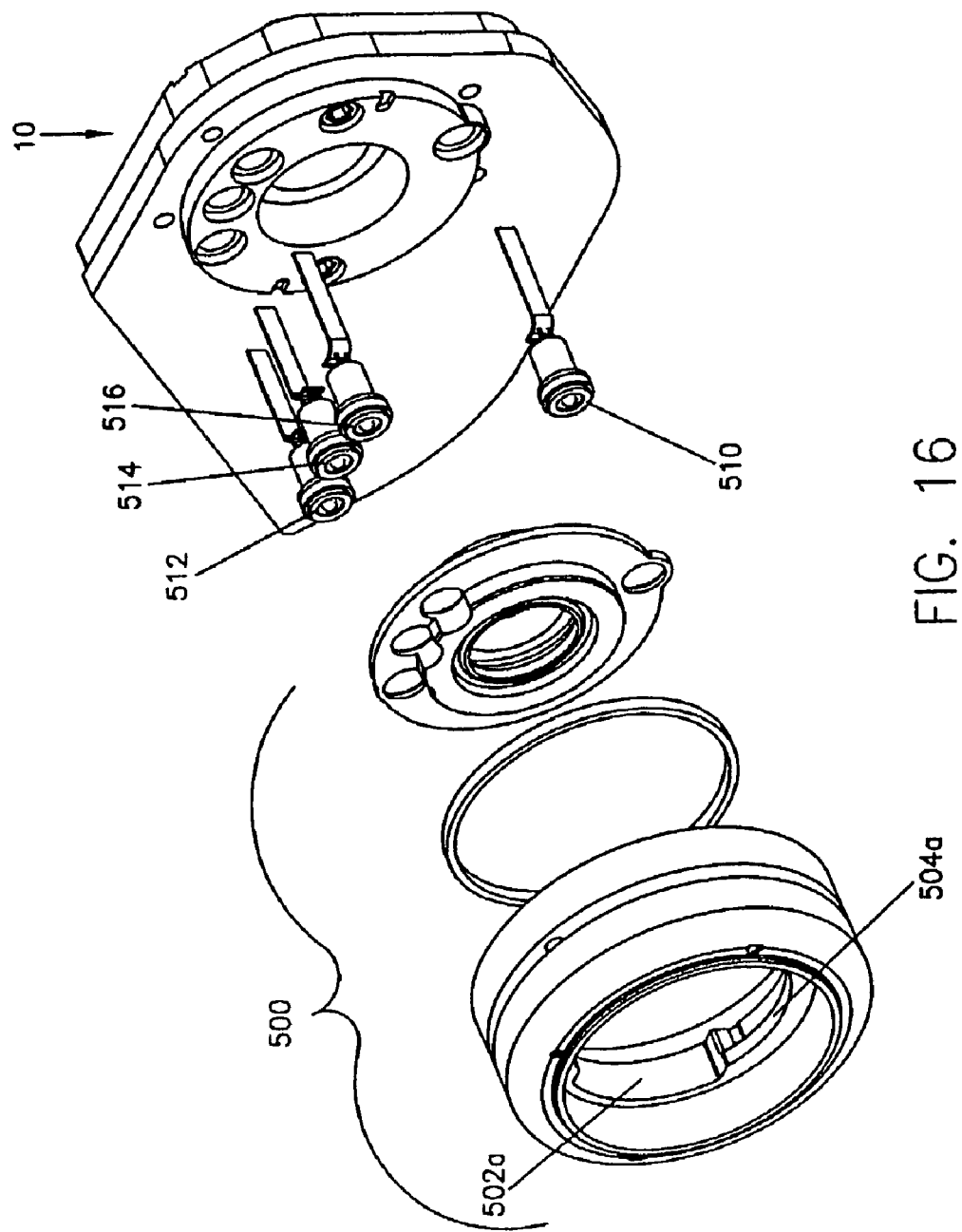
FIG. 16 is an exploded perspective view of an alternative injector head used in connection with the adapter embodiment shown in FIGS. 10 and 11.

As more fully described in U.S. Pat. No. 5,383,858, front-loading injectors have an injector head, including a front wall and an opening formed therein, and a drive member, such as a piston having a piston head, reciprocally mounted within the injector head and extendible through the injector head. In one embodiment of the present invention, as shown in FIGS. 1 and 2, the front-loading injector head 10 includes a front wall 12 and an opening 14 formed therein, a drive member, such as piston 16 having a piston head 18, and an injector face plate 20 removably mountable to front wall 12. Face plate 20 includes a releasable mounting mechanism, such as ears 22a and 22b (not shown), for attaching the face plate 20 to front wall 12. Specifically, ears 22a and 22b are inserted into opening recesses 14a and 14b, respectively, and face plate 20 is rotated 90 degrees such that ears 22a and 22b are engaged behind front wall protrusions 12a and 12b. Similarly injector face plate 20 is removed from the injector head 10 by rotating the face plate 20 90 degrees in the opposite direction and then removing ears 22a and 22b from opening recesses 14a and 14b. A gasket 24 is positioned between face plate 20 and front wall 12. A removable pin 26 is provided to keep face plate 20 from rotating with respect to front wall 12. Pin 26 is inserted into pin holes 21 and 13 located in the face plate 20 and front wall 12, respectively, and includes recess 28 for receiving and retaining tubing (not shown) that may be connected to the syringe. Face plate 20 is configured to accept a front-loading syringe 30 having a plunger 32, as described in U.S. Pat. No. 5,383,858. FIGS. 3–9 show the details of one embodiment of the adapter 100 of the present invention, which permits use of syringes of various types, sizes and configurations to be used with a front-loading injector having a removable injector face plate 20. For example, a syringe 40 which may be used with the adapter 100 may include a body 42, a flange 44 disposed at the distal end of the body 42, and a plunger 46 reciprocally mounted within body 42. Plunger 46 may also include internal screw threads (not shown) extending inwardly into the plunger 46 from the distal end of the plunger 46. As shown in FIGS. 5–9, adapter 100 includes an adapter face plate 120 having a releasable mounting mechanism, such as ears 122a and 122b, for attaching the adapter face plate 120 to a front load injector 10. The operation of ears 122a and 122b of adapter face plate 120 with injector opening recesses 14a and 14b (shown in FIG. 3) is similar to that of ears 22a and 22b of injector face plate 20 with injector opening recesses 14a and 14b, as previously described. Gasket 24 is provided between adapter face plate 120 and the injector front wall 12. In one embodiment, a detent 125, shown in FIG. 9, is provided on the distal surface of ear 122b, which cooperates with a groove (not shown) located in injector front wall protrusion 12b when the adapter face plate 120 is installed on injector front wall 12. The purpose of detent 125 and groove is to prohibit the operator from installing the adapter face plate 120 on the injector front wall 12 upside down. Adapter 100 further includes a reducing sleeve 140 formed of a reducing base 160 and reducing edge 180 connected to the proximal surface of base 160. Edge 180 and base 160 cooperate to form a recess 190 for receiving the distal flange 44 of syringe 40. Reducing base 160 is secured within adapter face plate 120 and includes an opening 170, which permits forward and reverse movement of the injector piston 16 of injector 10. Reducing edge 180 is preferably made from a material having a low coefficient of friction to facilitate easy and smooth movement of the syringe attachment mechanism such as locking pivot arms 220 and 240 pivotally attached to the proximal surface of edge 180, as described below. In the present invention, the syringe attachment mechanism may include locking pivot arms 220 and 240 pivoting at points 260 and 280, respectively, to releasably engage syringe flange 44. In one embodiment, as shown in FIGS. 5 and 9, pivot points 260 and 280 comprise a gear link 270 formed of adjoining gears 262 and 282 which cooperate with one another to permit simultaneous movement of arms 220 and 240 when only one arm 220 or 240 is grasped by the operator to move the arms 220 and 240 into an opened or closed position. It is understood, however, that the adapter 100 can be designed such that pivot arms 220 and 240 operate independently of one another, that only one arm moves, or that the adapter 100 only has one pivot arm. As shown in FIGS. 6 and 7, the inside surface of each pivot arm 220 and 240 includes first beveled surfaces 223 and 225, respectively, to permit reception of the syringe flange 44 when pivot arms 220 and 240 are in an open position, as shown in FIG. 6, and second beveled surfaces 227 and 229, respectively, to engage the distal end of the syringe body 42 when the pivot arms 220 and 240 are in a closed position, as shown in FIG. 7, and as more fully described below. Pivot arms 220 and 240 also include arm extensions 222 and 242, respectively, which assist in gripping and moving the pivot arms 220 and 240 into closed and opened positions. Pivot arm ends opposite pivot points 260 and 280 are cammed to engage and lock around lock point 300 extending from reducing edge 180. Lock point 300 includes a gasket 302, which assists in locking pivot arms 220 and 240 in place. It is understood that the syringe attachment mechanism may be of any configuration depending on the type, size and configuration of the particular syringe desired to be attached to the injector head 10. For example, if a syringe of a reduced diameter included radially projecting flanges, as shown in U.S. Pat. No. 5,383,858, the corresponding syringe attachment mechanism could be radially projecting retaining flanges, as shown in U.S. Pat. No. 5,383,858, that engaged the radially projecting flanges of the syringe. FIGS. 3, 12 and 13 further show that the adapter 100 includes a piston extension 320 provided for extending piston 16 for engagement with plunger 46 of syringe 40. This embodiment of the piston extension 320 includes means for joining the extension 320 to the base of the syringe plunger 46, such as screw threads 330 mateable with screw threads (not shown) formed at the distal end of the plunger 46. Piston extension 320 further includes protrusion 340 for attaching extension 320 to the piston head 18 via slot 19 located therein. Piston extensions of various diameters and lengths are used to permit use of syringes having various inner diameters and plunger locations. It is understood that alternative mechanisms can be designed to attach the piston extension to the injector drive piston and syringe plunger, depending on the configuration of the injector drive piston head and the particular syringe plunger. Similar to the injector face plate 20 of FIGS. 1 and 2, adapter face plate 120 is provided with a removable pin 124 to prohibit adapter face plate 120 from rotating with respect to front wall 12. Pin 124 is inserted into pin holes 123 and 13 located in adapter face plate 120 and injector front wall 12, respectively. Pin 124 further includes recess 126 for receiving and retaining tubing (not shown) that may be connected to the syringe 40. The adapter face plate 120 and injector head 10 may also include cooperating means for indicating to the injector head 10 that the adapter face plate 120 is properly attached to the injector head 10. Further, the cooperating means may also automatically calibrate the injector head 10 to adjust, for example, flow rate and pressure when an adapter face plate 120 is attached to the injector head 10. For example, as shown in FIG. 9, such cooperating means may include a plurality of magnetic points 340 through 350 at the distal surface of the adapter face plate 120. The injector head 10 includes two corresponding magnetic sensors 351 and 353, shown in FIG. 3, which recognize the presence of the magnetic points 344 and 346 when the adapter face plate 120 is properly attached. If magnetic sensors 351 and 353 do not sense magnetic points 344 and 346, or the magnetic points 340 through 350 are otherwise misaligned, the injector head 10 will not operate. To use the adapter shown in FIGS. 3–9, injector face plate 20 of FIG. 1 is removed, as previously described, and the adapter face plate 120 is attached to the front wall 12 of injector 10 by inserting ears 122a and 122b into opening recesses 14a and 14b, and rotating adapter face plate 120 90 degrees, as previously described. Pin 124 is then inserted into aligned pin holes 123 and 13. Piston extension 320 corresponding to a particular syringe 40 is attached to the injector piston 16 via protrusion 330 and slot 19. Pivot arms 220 and 240 are opened via arm extension 222 and 242 so that recess 190 of reducing sleeve 140 can receive the distal syringe flange 44. The plunger of the desired syringe 40 is then attached to the piston extension 320 via screw threads 330 such that the syringe flange 44 is received in recess 190. Once the syringe flange 44 is in place, pivot arms 220 and 240 are pivoted to a closed position, locking against lock point 300 and gasket 302, thus securing syringe 40 to adapter 100. The reverse process is followed to remove the syringe from the adapter 100. FIGS. 10 and 11 show another embodiment of the adapter 400. FIG. 10 is an exploded front view of the adapter 400 and FIG. 11 is an exploded back view of the adapter 400. In this embodiment, the injector head 10 does not include a removable face plate, as previously described in FIGS. 1 and 2. Instead, injector head 10, as shown in FIG. 16, includes a syringe receiving port 500 configured with recesses 502a and 502b (not shown), and retaining flanges 504a and 504b (not shown) to receive a syringe having radially extending distal flanges, as described in U.S. Pat. No. 5,383,858, or the adapter 400 of FIGS. 10 and 11. In particular, adapter 400 includes a reducing sleeve 140 attached to an adapter base 402 having ears 404a and 404b which cooperate with recesses 502a and 502b, and retaining flanges 504a and 504b of the syringe receiving port 500, to permit easy attachment and removal of the adapter 400 to the front wall 12 of the injector head 10. If adapter 400 is properly attached to the syringe receiving port 500, detent 410 of ear 404b activates sensor 510 of the injector head 10, shown in FIG. 16, thus indicating to the injector head 10 that the adapter 400 is attached to the injector head 10. Activation of sensor 510 may also automatically calibrate the injector head to adjust, for example, flow rate and pressure. When adapter 400 is not attached to the syringe receiving port 500, other sensors 512, 514, and 516 may be provided in injector head 10 to cooperate with syringe protrusions or detents when a syringe is inserted into the syringe receiving port 500 to indicate that the particular syringe is installed correctly and to identify its type, size and configuration. Operation of these sensors, protrusions and detents is similar to the sensors, protrusions and detents described in U.S. Pat. No. 5,383,858. Other adapter elements previously described with respect to FIGS. 3–9, particularly the syringe attachment mechanism, may be included in this embodiment. Another embodiment of a piston extension 550 is shown in FIGS. 14 and 15. In this embodiment, the corresponding injector drive piston 600 includes a piston head 610 having an attachment flange 612 for insertion into a corresponding slot 570 located at a first end of the piston extension 550. Spring loaded pin 580 located within slot 572 engages recess 614 of the attachment flange 612 when the piston extension 550 is properly attached to the piston drive head 610, thus prohibiting the accidental dislodgment of the piston extension 550 from the piston drive head 610. A second end of the piston extension includes means for securing the piston extension to the plunger, such as screw threads 560. Although the syringe adapters of the invention have been described in detail for the purpose of illustration, it is to be understood that such detail is solely for that purpose and that variations can be made thereto by those skilled in the art without departing from the spirit and scope of the invention.

The invention claimed is:

1. An adapter for connecting a syringe comprising a plunger to an injector comprising a drive piston, the adapter comprising: a piston extension having a first end and a second end, the first end comprising a first connector member adapted to be connected to the drive piston and a second end comprising a second connector member adapted to be connected to the plunger of the syringe, the first connector member defining a slot having an opening on the side of the first connector and being mateable with an attachment flange formed on the drive piston, the first connector member further comprising a pin located within the slot and operable to engage a recess formed in the attachment flange of the drive piston.

2. The adapter of claim 1 wherein the second connector member comprises threads mateable with threads formed on the plunger of the syringe.

3. The adapter of claim 2 wherein the threads on the second connector members are external threads.

4. The adapter of claim 1 wherein the pin is spring-loaded.

5. The adapter of claim 1, further comprising an adapter face plate for attaching the syringe to the injector.

6. The adapter of claim 5 wherein the adapter face plate comprises a mounting device for attaching the adapter face plate to the injector.

7. The adapter of claim 6 wherein the mounting device comprises at least one mounting ear.

8. The adapter of claim 7 wherein the at least one mounting ear comprises two mounting ears.

9. The adapter of claim 8 wherein the two mounting ears are positioned in substantially opposed relation to one another.

10. The adapter of claim 7 wherein the at least one mounting ear is adapted to be engaged with at least one protrusion formed on the injector to attach the adapter face plate to the injector.

11. The adapter of claim 10 wherein the at least one mounting ear comprises two mounting ears and the at least one protrusion comprises two protrusions, and further wherein each of the two mounting ears is operable to be rotated into engagement with a respective one of the two protrusions to attach the adapter face plate to the injector.

12. The adapter of claim 5 wherein the adapter face plate comprises an attachment mechanism adapted to removably mount the syringe to the injector.

13. The adapter of claim 12 wherein the attachment mechanism comprises a base defining a recess for receiving at least one flange of the syringe.

14. The adapter of claim 12 wherein the attachment mechanism comprises a base for receiving the syringe and a pair of pivoting arms attached to the base and movable from an opened position to a closed position to engage the syringe.

15. The adapter of claim 14 wherein the attachment mechanism further comprises a locking member extending from the base to secure the pair of pivoting arms in the closed position after the syringe is received by the base.

16. The adapter of claim 14 wherein the pair of pivoting arms is attached to the base by a gear mechanism.

17. The adapter of claim 16 wherein the gear mechanism permits simultaneous movement of the pivoting arms.

18. The adapter of claim 14 wherein each of the pivoting arms comprises a first beveled surface to permit reception of the syringe when the pivoting arms are in the opened position.

19. The adapter of claim 18 wherein each of the pivoting arms comprises a second beveled surface to engage the syringe when the pivoting arms are in the closed position.

20. The adapter of claim 14 wherein each of the pivoting arms comprises an arm extension to assist in moving the pivoting arms.

21. The adapter of claim 5 wherein the adapter face place defines an opening therein through which the drive piston and the piston extension are extendable.

22. The adapter of claim 6, further comprising at least one device adapted to cooperate with at least one sensor on the injector when the adapter face plate is attached to the injector.

23. The adapter of claim 22 wherein the at least one device cooperates with the at least one sensor to indicate that the adapter face plate is attached to the injector.

24. The adapter of claim 22 wherein the at least one device cooperates with the at least one sensor to calibrate at least one operating parameter of the injector.

25. The adapter of claim 24 wherein the at least one operating parameter comprises one or more of flow rate and pressure.

26. The adapter of claim 22 wherein the at least one device comprises a plurality of devices and the at least one sensor comprises a plurality of sensors.

27. The adapter of claim 22 wherein the at least one device comprises a detent.

28. The adapter of claim 22 wherein the at least one device comprises a signal generator.

29. The adapter of claim 22 wherein the at least one device is disposed on the at least one mounting device.

30. An adapter for connecting a syringe comprising a plunger to an injector comprising a drive piston and at least one sensor, the adapter comprising:
    a piston extension having a first end and a second end, the first end comprising a first connector member adapted to be connected to the drive piston and a second end comprising a second connector member comprising threads mateable with and adapted to be connected to threads formed on the plunger of the syringe;
    an adapter face plate for attaching the syringe to the injector, the adapter face plate comprising a mounting device for attaching the adapter face plate to the injector and an attachment mechanism adapted to removably mount the syringe to the injector; and
    at least one device adapted to cooperate with at least one sensor on the injector when the adapter face plate is attached to the injector.

31. The adapter of claim 30 wherein the first connector member defines a slot mateable with an attachment flange formed on the drive piston.

32. The adapter of claim 31 wherein the first connector member further comprises a pin located within the slot and operable to engage the attachment flange of the drive member.

33. The adapter of claim 30 wherein the mounting device comprises at least one mounting ear.

34. The adapter of claim 33 wherein the at least one mounting ear comprises two mounting ears.

35. The adapter of claim 34 wherein the two mounting ears are positioned in substantially opposed relation to one another.

36. The adapter of claim 33 wherein the at least one mounting ear is adapted to be engaged with at least one protrusion formed on the injector to attach the adapter face plate to the injector.

37. The adapter of claim 30 wherein the attachment mechanism comprises a base defining a recess for receiving at least one flange of the syringe.

38. The adapter of claim 30 wherein the attachment mechanism comprises a base for receiving the syringe and a pair of pivoting arms attached to the base and movable from an opened position to a closed position to engage the syringe.

39. The adapter of claim 38 wherein the pair of pivoting arms is attached to the base by a gear mechanism.

40. The adapter of claim 39 wherein the gear mechanism permits simultaneous movement of the pivoting arms.

41. The adapter of claim 30 wherein the adapter face place defines an opening therein through which the drive piston and the piston extension are extendable.

42. The adapter of claim 30 wherein the at least one device cooperates with the at least one sensor to indicate that the adapter face plate is attached to the injector.

43. The adapter of claim 30 wherein the at least one device cooperates with the at least one sensor to calibrate at least one operating parameter of the injector.

44. The adapter of claim 30 wherein the at least one device comprises a plurality of devices and the at least one sensor comprises a plurality of sensors.

45. The adapter of claim 30 wherein the at least one device comprises a detent.

46. The adapter of claim 30 wherein the at least one device comprises a signal generator.

47. The adapter of claim 30 wherein the at least one device is disposed on the at least one mounting device.

48. An adapter for connecting a syringe comprising a plunger to an injector comprising a drive piston and a sensor, the adapter comprising:
    a piston extension having a first end and a second end, the first end comprising a first connector member defining a slot adapted to be engaged with an attachment flange formed on the drive piston and a second end comprising a second connector member comprising threads mateable with and adapted to be connected to threads formed on the plunger of the syringe;

an adapter face plate for attaching the syringe to the injector, the adapter face plate comprising two mounting ears positioned in substantially opposed relation to one another for attaching the adapter face plate to the injector and an attachment mechanism defining a recess for receiving at least one flange of the syringe to removably mount the syringe to the injector; and a device on at least one of the two mounting ears, the device adapted to cooperate with the sensor on the injector when the adapter face plate is attached to the injector.

49. The adapter of claim 48 wherein the adapter face place defines an opening therein through which the drive piston and the piston extension are extendable.

50. The adapter of claim 48 wherein the device cooperates with the sensor to indicate that the adapter face plate is attached to the injector.

51. The adapter of claim 48 wherein the device cooperates with the sensor to calibrate at least one operating parameter of the injector.

52. The adapter of claim 48 wherein the device comprises a plurality of devices and the sensor comprises a plurality of sensors.

53. The adapter of claim 48 wherein the device comprises a detent.

54. An adapter for connecting a syringe comprising a plunger to an injector comprising a drive piston, the adapter comprising: a piston extension having a first end and a second end, the first end comprising a first connector member adapted to be connected to the drive piston and a second end comprising a second connector member adapted to be connected to the plunger of the syringe, the first connector member defining a slot mateable with an attachment flange formed on the drive piston, the first connector member comprising a pin located within the slot and being operable to engage a recess formed in the attachment flange of the drive piston.

55. The adapter of claim 54 wherein the pin is spring-loaded.

* * * * *